United States Patent

Podesva et al.

[11] 3,966,761
[45] June 29, 1976

[54] NOVEL AMINO-INDAZOLE COMPOUNDS

[75] Inventors: Ctirad Podesva, Montreal; William T. Scott, Chateauguay, both of Canada

[73] Assignee: Delmar Chemicals Limited, Ville La Salle, Canada

[22] Filed: Feb. 7, 1974

[21] Appl. No.: 440,445

[30] Foreign Application Priority Data

Feb. 7, 1973    United Kingdom.................. 6030/73

[52] U.S. Cl............................ 260/310 C; 260/311; 424/273
[51] Int. Cl.²............... C07D 231/56; A61K 31/415; A01N 9/22
[58] Field of Search........................ 260/310 C, 311; 203/477, 448

[56] References Cited

UNITED STATES PATENTS 3,318,905   5/1967   Palazzo .......................... 260/310 C
3,767,670   10/1973  Podesva et al. ................. 260/310 C

FOREIGN PATENTS OR APPLICATIONS 739,485   7/1966   Canada ........................... 260/310 C

OTHER PUBLICATIONS

Kataoka et al., Chem. Pharm. Bull. vol. 19, pp. 1511–1513 (1971) (July) RS1.C4.
Palazzo et al., J. Med. Chem. vol. 9, pp. 38–41 (1966) RS1.J5.

Primary Examiner—Donald B. Moyer
Attorney, Agent, or Firm—Christen & Sabol

[57] ABSTRACT

This invention provides novel tertiary aminoindazole compounds of the following general formula:

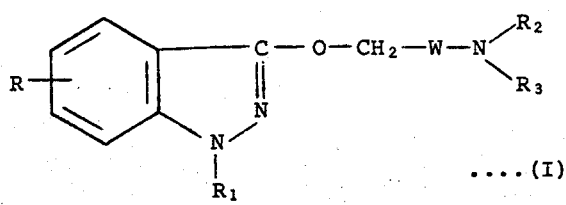

.... (I)

wherein R represents a hydrogen or halogen atom; $R_1$ represents an alkyl group, a substituted or unsubstituted aryl group or a substituted or unsubstituted aralkyl group; $R_2$ and $R_3$ both represent a lower alkyl or aralkyl group and W represents a branched chain alkylene group, and salts, especially acid addition and quaternary ammonium salts thereof, and processes for making them. Such compounds are pharmacologically active in that they exhibit antiinflammatory and analgesic effects so the invention also provides pharmaceutical compositions containing one or more of these compounds as the active ingredient. They are also useful anti-microbial agents.

8 Claims, No Drawings

NOVEL AMINO-INDAZOLE COMPOUNDS

BACKGROUND TO THE INVENTION a. Field of Invention

This invention relates generally to novel tertiary amino-indazole compounds, to pharmaceutical compositions containing such compounds and to processes for making them. More particularly, this invention is concerned with novel tertiary amino-indazole compounds having the following general formula:

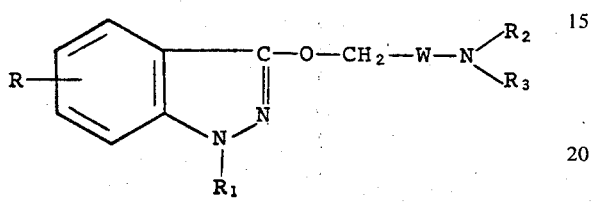

.... (I)

wherein R represents a hydrogen or halogen atom; $R_1$ represents an alkyl group, a substituted or unsubstituted aryl group or a substituted or unsubstituted aralkyl group; $R_2$ and $R_3$ both represent a lower alkyl or aralkyl group and W represents a branched chain alkylene group and salts such as acid addition and quaternary ammonium salts thereof.

b. Prior Art

1-Substituted-3-dialkylaminoalkoxy-1H-indazole compounds of the following general formula:

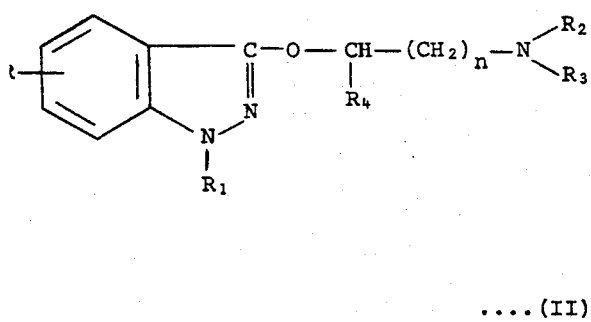

.... (II)

wherein R, $R_1$, $R_2$, and $R_3$ have the same significance as in Formula I hereinbefore, $R_4$ represents a hydrogen atom or an alkyl group, and n is 1 or 2, have been described in the prior art, for example, U.S. Pat. No. 3,318,905 issued in 1967 to Angelini Francesco of Italy. This specification describes the preparation of such compounds by a Williamson's type synthesis similar to that described previously in the art (cf. Name Reactions in Organic Synthesis, 2nd Edition, Academic Press - 1961) and involving, in general terms, the introduction of a preformed dialkylaminoalkyl side chain into the 3-position of an oxy-indazole compound containing appropriate substituents R and $R_1$. More specifically, as described in the aforementioned specification, the synthesis of the desired indazole compounds of the general formula II is accomplished by reacting an appropriately substituted 3-hydroxy-1H-indazole having the following general formula:

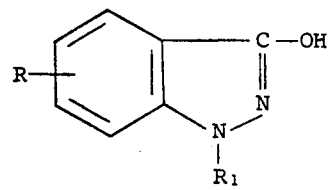

.... (III)

advantageously in the form of an alkali metal salt, say the sodium or potassium salt, with a halogeno-alkyldialkylamine compound having the following general formula:

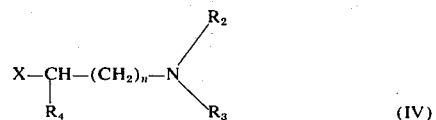

(IV)

wherein R, $R_1$, $R_2$, $R_3$, $R_4$, and n have the same significance as specified hereinbefore and X represents a halogen atom, typically a chlorine atom. The reaction is usually conducted by heating the reactants together in an inert solvent, say xylene or toluene. In a variant of this prior art process described, for instance, in Dutch patent application No. 68/17852 published in 1969 to Egyesult Gyogyszer, the halogen atom in the halogenoalkyl-dialkylamine of the general formula IV may be replaced by other suitable leaving groups such as, for example, as a mesyl, tosyl, phenylsulfonate or p-bromophenylsulfonate group and the process involves the reaction of the corresponding 3-hydroxy-1H-indazole in the form of its sodium salt with the α-substituted alkyl-dialkylamine.

As described in the aforementioned United States patent specification, indazole compounds embraced by the foregoing general formula II are biologically active in that some manifest analgesic, antiinflammatory and myorelaxing activity. Probably the best known of such compounds at the present time is 1-benzyl-3-[3-(dimethylamino)propoxy]-1H-indazole, commonly referred to as benzydamine, which in the form of the hydrochloride salt, is employed in chemotherapy as an analgesic, antipyretic and/or antiinflammatory agent. In this role, the benzydamine hydrochloride is asssociated in pharmaceutical compositions with pharmaceutically acceptable organic or inorganic, solid or liquid carriers. According to the process described in the aforementioned United States specification, this compound is prepared by heating the sodium salt of 1-benzyl-3-hydroxy-1H-indazole with 3-chloropropyldimethylamine in xylene as an inert solvent. Treatment of the 1benzyl-3-[3-(dimethylamino)propoxy]-1H-indazole so-obtained with ethereal hydrochloric acid yields the corresponding hydrochloride salt, with a melting point of 160°C.

Whilst the tertiary amino-indazole compounds of the foregoing general formula II are known, tertiary aminoindazole compounds of the foregoing general formula I, characterized by the presence of a branched chain alkylene group bearing substituent alkyl groups attached from carbon atoms β or γ to the oxygen atom, are novel compounds not specifically described in or covered by the claims of the aforementioned United States patent specification, nor are they referred to elsewhere in the literature.

STATEMENTS OF INVENTION

According to this invention in one of its product aspects there are provided tertiary amino-indazole compounds having the following general formula:

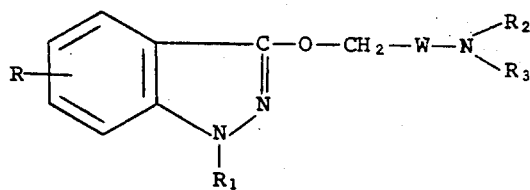

.... (I)

wherein R, $R_1$, $R_2$, $R_3$, and W have the same significance as hereinbefore and salts, especially acid addition and quaternary ammonium salts thereof. Preferred aminoindazole compounds of the foregoing general formula I are those in which:

R represents a hydrogen or chlorine atom;
$R_1$ represents a lower aralkyl group such, for example, as benzyl;
$R_2$ and $R_3$, which may be the same or different, each represents methyl or ethyl; and
W represents a group of the following formula:

As used herein the term lower in the context of alkyl and aralkyl connotes an alkyl moiety containing from 1 to 6 carbon atoms inclusive such, for example, as methyl, ethyl, propyl, isopropyl, n-butyl, isobutyl, tert. butyl, amyl, and hexyl. As used herein the term branched chain lower alkylene in the context of W connotes branched chain hydrocarbon groups having from two to ten carbon atoms comprising a divalent straight chain lower alkyl radical with a lower alkyl group pendant from the carbon atom located β or γ to the oxygen atom.

A highly preferred class of compounds are the 1-benzyl-3-[(2-ethyl-2-dimethylamino)ethoxy]-5 or 6R-1H-indazoles, of the following general formula:

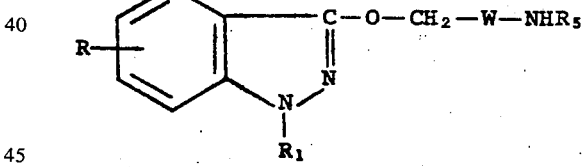

.... (I')

wherein R has the same significance as hereinbefore. Representative compounds within this preferred class are: 1-benzyl-3-[(2-ethyl-2-dimethylamino)ethoxy]-5-chloro-1H-indazole, 1-benzyl-3-[(2-ethyl-2-dimethylamino)ethoxyl]-6-chloro-1H-indazole and 1-benzyl-3-[(2-ethyl-2-dimethylamino)ethoxy]-1H-indazole and salts, particularly acid addition salts thereof.

Representative compounds falling within the scope of formula I have been found to possess antiinflammatory and analgesic activity when tested pharmacologically by experimental and scientifically acceptable procedures in mice.

According to this invention in a process aspect, there is provided a process for preparing the tertiary amino-indazoles of the foregoing general formula I comprising the N-alkylation, using known procedures, of a corresponding primary or secondary amine in the form of an amino-indazole compound of the following general formula:

.... (VI)

wherein R, $R_1$ and W have the same significance as in formula I hereinbefore and $R_5$ represents a hydrogen atom or a lower alkyl group in the form of the free base or an acid addition salt thereof.

The term known as applied to the N-alkylation reaction in this specification refers to methods presently or heretofore in actual use and/or described in the literature on the subject. Also, the N-alkylation may be mono or di-alkylation, depending upon whether the amino-indazole compound of the formula VI above is a primary or secondary amine, with the introduction of one or two alkyl substituents as the case may be.

The primary and secondary amino-indazole compounds of the foregoing formula VI are further described together with processes for making them in the specification of our British application No. 55232/72 and D.O.S. No. P 2258694.3. Similar processes which, with the use of suitable starting compounds, may be used to prepare the compounds of formula VI are described in copending U.S. Pat. application Ser. No. 203,477 filed Nov. 30, 1971 now abandoned. of an appropriately substituted phthalimidoalkoxy-1H-indazole employing, for example, hydrazine or hydrazine hydrate. Accordingly, therefore, this invention in another of its aspects provides a two step process for the preparation of the desired tertiary amino-indazoles of the foregoing general formula I involving:

A. dephthaloylation of an appropriately substituted phthalimidoalkoxy-1H-indazole followed, if desired, by conversion of the primary amine so-obtained into a secondary amine by N-alkylation; and B. N-alkylation of the primary or secondary amine by any suitable known procedure.

The phthalimidoalkoxy-1H-indazole compounds themselves are also described along with processes for preparing them in the specification of the aforementioned copending application. Accordingly, therefore, this invention in another of its aspects provides a three step process for the preparation of the desired tertiary amino-indazoles of the foregoing general formula I involving:

A. initial preparation of an appropriately substituted phthalimidoalkoxy-1H-indazole;

B. dephthaloylation of said phthalimidoalkoxy-1H-indazole followed, if desired, by conversion of the primary amine so-obtained into a secondary amine by N-alkylation of any suitable known procedure; and C. N-alkylation of the primary or secondary amine by any suitable known procedure.

DETAILED DESCRIPTION OF THE INVENTION

The primary and secondary amino-indazole starting compound of the general formula VI for the N-alkylation process of this invention may be used in the form of the free base or as a salt, for instance, as an acid addition salt with a mineral acid such as hydrochloric acid. Conveniently, it is used in the form of the free base.

The N-alkylation procedure may be any one of a variety of standard known procedures. The term known as applied to the N-alkylation reaction in this specification and appended claims refers to methods presently or heretofore in actual use and/or described in the literature on the subject. Also, the N-alkylation may be mono or dialkylation, depending upon whether the amino-indazole compound II is a primary or secondary amine, with the introduction of one or two alkyl or aralkyl substituents as the case may be. The method of choice in a particular instance depends to some extent on the nature of the primary or secondary amino-indazole starting compound and the end product desired.

For instance, the tertiary amine may be obtained by a direct alkylation procedure involving treatment of the indazole compound VI with an alkylating agent which is an ester of an aliphatic or araliphatic alcohol having the formula $R^1-OH^1$, with a strong organic or inorganic acid, said ester having the formula $R^1-An^1$, where $An^1$ is the anion of the strong acids. These agents include, for example, methyl iodide, methyl bromide, methyl p-toluenesulfonate, dimethyl sulfate, ethyl iodide, ethyl p-toluenesulfonate, n-propyl iodide, and the like. It will be appreciated that when a primary amine of the general formula VI is used as the starting compound, two moles of the ester, $R^1-An^1$, conveniently added in a single step, are required to form the desired tertiary amine; on the other hand, when a secondary amine of the general formula VI is used as the starting compound, one mole of the ester is all that is required. Such an alkylation reaction is conveniently conducted by mixing the selected amine with one or two molecular equivalents of the ester, $R^1-An^1$, as required, plus an excess of the ester if desired. Depending upon the nature of the reactants, such an alkylation procedure can be conducted in the absence of any solvent other than the reactants themselves or can be conducted in the presence of an organic solvent such, for example, as a lower aliphatic alcohol like ethanol, methanol or isopropanol, or an aromatic hydrocarbon like benzene or xylene. The reaction of the ester with the amine can be facilitated by heating the reaction mixture.

Alternatively, the N-alkylation may be accomplished by a reductive alkylation procedure in which a primary or secondary amino-indazole having the general formula VI is initially reacted with an appropriate carbonyl compound such as an aldehyde, ketone or ester followed by reduction to give the secondary or tertiary amine respectively; thereafter, the secondary amine may be converted into the desired tertiary amine. This reduction may be effected, for example, by catalytic hydrogenation using hydrogen and, say, a palladium on charcoal, platinum or Raney nickel catalyst, by a metal hydride or by formic acid or one of its derivatives. For instance, a Schiff's base may be obtained by reacting a primary amine with a carbonyl compound, say, an aliphatic aldehyde such, for example, as acetaldehyde. Conveniently, this reaction is conducted in an organic solvent such as an aromatic hydrocarbon, for example, benzene or toluene, a halogenated hydrocarbon such as a chlorobenzene, an ether such as an ethyl ether or dibutyl ether, a lower aliphatic alcohol such as methanol, ethanol or 2-ethoxy ethanol and the like. While temperature and pressure are not critical aspects of this particular process leading to a Schiff's base, it is preferred to effect the reaction at elevated temperatures, preferably at from about 50°C. to 150°C., and conveniently at the reflux temperature of the solvent. If desired, the Schiff's base so-obtained may be reduced in situ to the desired secondary amine. Conveniently, however, it is isolated from the reaction medium then subsequently reduced. Lithium aluminum hydride or sodium borohydride are excellent for this reduction, although catalytic hydrogenation with hydrogen and, for example, palladium on charcoal, or, indeed, any one of a number of means of reduction known to the art can be used. The reduction can be carried out at room temperature or at temperatures below room temperature or with the application of heat depending upon the method elected. For instance, using sodium borohydride, it is preferably carried out by heating the reaction mixture under reflux. The reduction is preferably carried out in an organic solvent such, for example, as methanol, ethanol, dioxane or tetrahydrofuran.

In conjunction with the above alkylation procedures, a secondary amine may also be obtained, via the Schiff's base intermediate, by employing an aromatic aldehyde such, for example, as benzaldehyde as the carbonyl compound. The Schiff's base so-formed by condensation of amine and benzaldehyde is then reacted with a lower alkyl halide, such as methyl or ethyl bromide, to form a quaternary ammonium salt. This salt is then hydrolyzed to yield the desired lower alkyl secondary amine and benzaldehyde. The secondary amine so formed can then be further alkylated to give the desired tertiary amine.

In an alternative reductive alkylation procedure, the primary or secondary amine is acylated, for instance, with an acyl halide or acid anhydride to give a 3-N-acylaminoalkoxy-1H-indazole or a 3-N,N-diacylaminoalkoxy-1H-indazole respectively which is then reduced to the corresponding 3-N-mono or 3-N,N-dialkylaminoalkoxy-1H-indazole compound; in the case of the 3-N-alkylaminoalkoxy-1H-indazole compound, this can be acylated again and reduced to give the desired tertiary amine.

A further reductive alkylation procedure which is the method of choice in preparing those tertiary amines in which $R_2$ and $R_3$ are both methyl, say, 1-benzyl-3-[(2-ethyl-2-dimethylamino)ethoxy]-1H-indazole, is provided by the Eschweiler-Clarke modification of the Leuckart reaction (Organic Reactions V. p. 301 - New York). In this reaction a primary amine, in the form of an acid addition salt thereof or, more conveniently, as the free base, is reacted with formaldehyde and formic acid. Advantageously, this reaction is conducted in excess of one or both of formic acid and formaldehyde to serve as the solvent. When the primary amine is used in the form of an acid addition salt, a base such, for example, as sodium acetate, (e.g. in an amount of 1 molar equivalent per mole amine) should desirably be included in the reaction medium to liberate the free base in which form it reacts. Typically, this reaction is conducted at an elevated temperature, for instance, between about 50°C. and 150°C., conveniently at the reflux temperature of the formic acid (ca. 100°C.).

Depending on the reaction conditions employed, the tertiary amino-indazole compound is obtained from the N-alkylation procedure in the form of the free base or an acid addition salt thereof. If it is obtained in the form of the free base it may be converted to acid addition salts by reaction with the selected acid conveniently in the presence of an organic solvent inert to the reactants under the conditions of reaction and under substantially anhydrous conditions. When the compounds are to be used as intermediates for preparing other compounds or for any other non-pharmaceutical application, the toxicity or non-toxicity of the salt is immaterial. When the compounds are to be used as pharmaceuticals, they are most conveniently used in the form of water-soluble, non-toxic acid addition salts. The acids which can be used to prepare the preferred non-toxic acid addition salts are those which produce, when combined with the free bases, salts whose anions are relatively innocuous to the animal organism in therapeutic doses of the salts, so that beneficial physiological properties inherent in the free bases are not vitiated by side-effects ascribable to the anions. Appropriate acid addition salts are those derived from mineral acids such as hydrochloric acid, hydrobromic acid, hydriodic acid, nitric acid, sulfuric acid and phosphoric acid; and organic acids such as acetic acid, citric acid, lactic acid, tartaric acid and maleic acid.

The acid addition salts are prepared, for example, by dissolving the free base in an aqueous solution containing the appropriate acid and isolating the salt by evaporating the solution, or by reacting the free base and the selected acid in an organic solvent, in which case the salt separates directly or can be obtained by concentration of the solution.

Alternatively, quaternary ammonium salts may be prepared by treating the free amine with lower alkyl and aralkyl esters of strong inorganic acids and organic sulfuric acids such, for example, as methyl chloride, methyl bromide, methyl iodide, ethyl bromide, propyl bromide, propyl iodide, benzyl chloride, benzyl bromide, methyl sulfate, methyl benzenesulfonate and methyl p-toluene sulfonate.

In the event the tertiary amino-indazole is obtained from the N-alkylation reaction in the form of the acid addition salt, the free base may be liberated therefrom by basification in the usual way.

A convenient N-alkylation procedure for preparing a preferred compound, 1-benzyl-3-[(2-ethyl-2-dimethylamino)-ethoxy]-1H-indazole hydrochloride, involves the N-methylation of 1-benzyl-3-[(2-ethyl-2-amino)ethoxy]-1H-indazole, either as the free base or an acid addition salt, say, hydrochloride salt, by reaction of this compound with aqueous formaldehyde and formic acid. The alkylation should desirably be conducted in the presence of a base such, for example, as sodium acetate, if the indazole compound is reacted in the form of the acid addition salt. Conveniently, this alkylation is conducted at an elevated temperature, say, the reflux temperature of formic acid. Thereafter, the reaction mixture is made basic, for instance, by the addition of aqueous alkali, for example, aqueous sodium hydroxide and the desired tertiary amine recovered by standard techniques, usually in the form of a viscous yellowish oil. The tertiary amine is then converted into the hydrochloride salt, for example, by addition of hydrogen chloride in ethyl acetate-methanol mixture or ether. The hydrochloride is recovered in the form of white crystals, which may be recrystallized, for example, from ethanol, or an ethyl acetate-methanol mixture to give a substantially pure product.

As previously mentioned herein, the 3-aminoalkoxy-indazole compounds of the foregoing general formula VI are novel compounds which are further described and claimed, together with processes for preparing them, in the specification of our said copending applications.

Briefly, they may be prepared from a 3-hydroxy-1H-indazole as the starting compound by a process involving:

A. formation of a corresponding 3-phthalimidoalkoxy-1H-indazole, typically by reaction of a 3-hydroxy-1H-indazole, conveniently in the form of an alkali metal salt, say, sodium salt thereof, with an N-(haloalkyl)-phthalimide; alternatively, the 3-phthalimidoalkoxy compound can be prepared by the reaction of an alkoxyindazole of the following general formula:

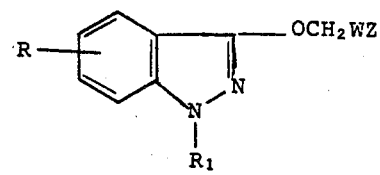

. . . . . . . VII' wherein

R and W have the same significance as hereinbefore and Z stands for a leaving group, with a phthalimide compound of the following general formula:

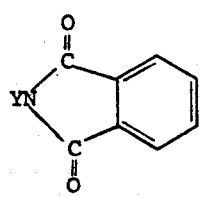

......VIII' wherein

Y represents a hydrogen atom or a monovalent cation. Conveniently the Z substituent in the formula VII' represents a halogen atom, for example, chloro, and the substituent Y in the formula VIII' represents an alkali metal cation, for example, sodium or potassium. The alkoxyindazole of the formula VII' can be readily prepared by reaction of the corresponding 3-hydroxyindazole with a compound of the formula Z'CH₂WZ wherein Z and Z' both represent different leaving groups and with Z' being more labile than Z, for example, Z can be a chlorine atom when Z' is a bromine atom.

B. dephthaloylation of the 3-phthalimidoalkoxy-1H-indazole to yield the corresponding 3-aminoalkoxy-1H-indazole; and C. optionally, conversation of the 3-aminoalkoxy-1H-indazole into an acid addition salt, say, the hydrochloride salt thereof.

The 3-phthalimidoalkoxy-1-H-indazole compounds are also novel and they are also described together with processes for preparing them in the specification of our aforementioned copending applications.

The overall process for preparing the desired tertiary amino-indazole compounds is illustrated in the following flow sheet:

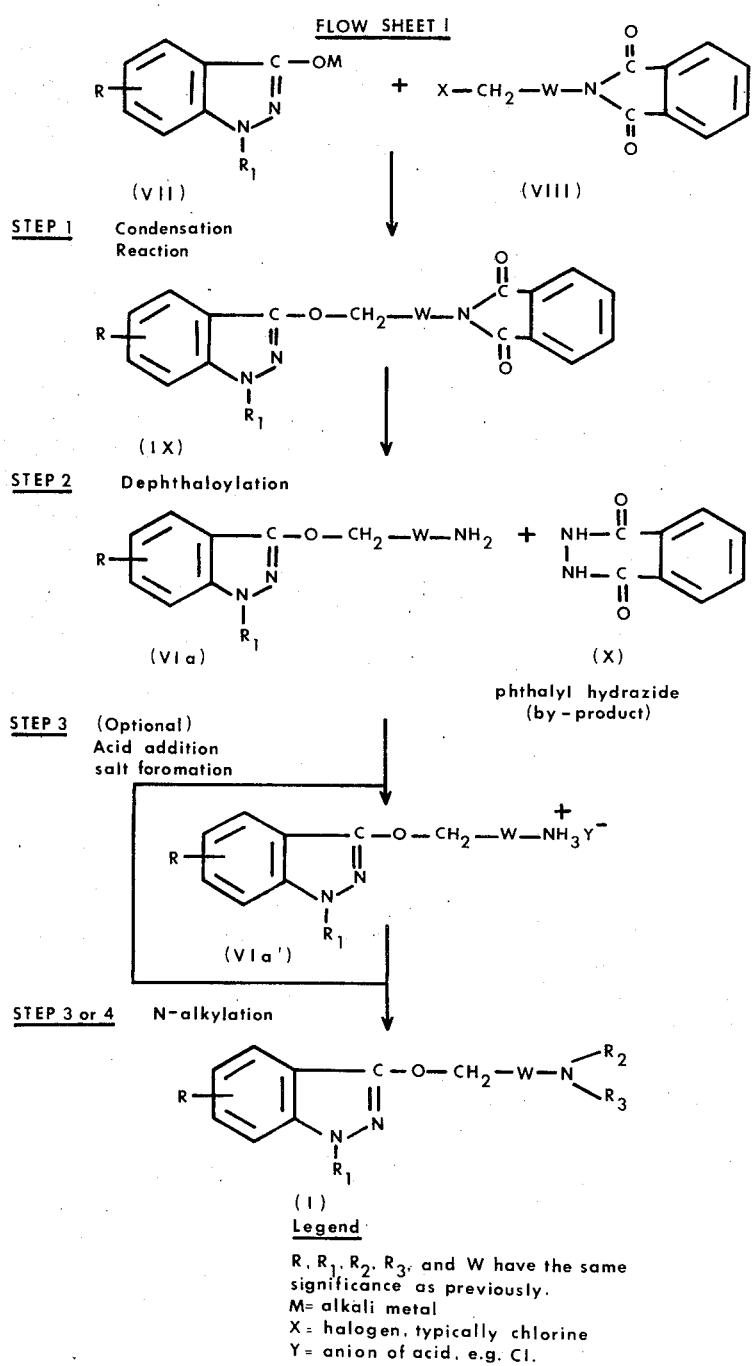

Representative 3-hydroxy-1H-indazole compounds of the foregoing general formula VII and metal salts thereof are known, being described, for instance, in Beilstein, Vol. XXIV, p. 113, and all may be readily obtained by standard procedures. For example, such compounds may be prepared from N-substituted anthranilic acid or esters of the general formula XI; the latter compounds are nitrosated, and the corresponding nitroso compounds reduced, with an alkali metal hydrosulfite, say, sodium or potassium hydrosulfite, to yield the alkali metal salt, say, the sodium or potassium salt respectively of 3-hydroxy-1H-indazole directly. This procedure is illustrated in the following flow sheet:

FLOW SHEET II

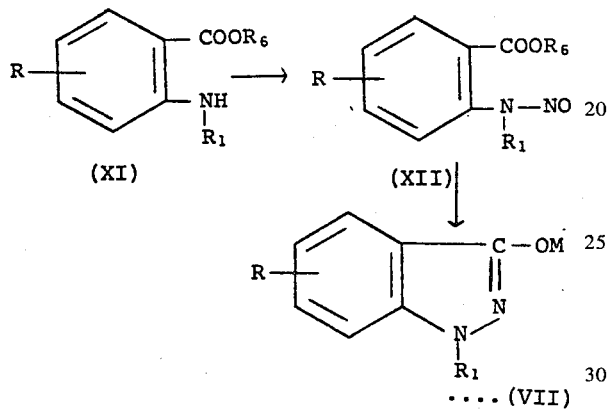

.... (VII)

In the reaction sequence shown in flow sheet II, R, $R_1$ and M have the same significance as hereinbefore and $R_6$ represents hydrogen or alkyl, preferably lower alkyl.

An alternative procedure for preparing the 3-hydroxy-1H-indazole compounds is basically similar to that described in Organic Synthesis, Collective Vol. 3, p. 475–479 starting from an anthranilic acid and proceeding throuogh a diazonium salt, which is converted into an o-hydrazinobenzoic acid hydrochloride which, in turn, is cyclized into the 3-hydroxy-1H-indazole compound.

The N-(haloalkyl)-phthalimides of the foregoing general formula VIII are also known compounds that can be readily obtained following standard procedures. For example, such compounds may be prepared by condensing an alkali or alkaline earth metal phthalimide, say, sodium or potassium phthalimide with an appropriate dihaloalkane conveniently using an excess of the dihaloalkane as solvent and conducting the reaction at the reflux temperature thereof. In an alternative and preferred procedure which affords the desired N-haloalkyl-phthalimide in good yield, an aminoalcohol, say, 2-aminobutan-1-ol is reacted with phthalic anhydride in an inert organic solvent such as benzene, toluene or xylene usually at an elevated temperature, say, reflux, and the hydroxy group in the resulting N-(hydroxyalkyl)-phthalimide converted into halogen by standard procedures, say, using phosphorus pentachloride or thionyl chloride.

The invention will be more completely understood from the specific examples which follow. These examples are set forth by way of illustrating a procedure for preparing representative tertiaty amino-indazoles provided by this invention and it will be understood that the invention is not to be construed as limited in spirit or scope by the details contained therein, as many modifications in materials and procedures will be readily apparent to those skilled in the art. In these examples, the melting point data is uncorrected and was obtained by the capillary tube method, and all temperatures are in degrees centigrade.

EXAMPLE 1

1-Benzyl-3-[(2-ethyl-2-dimethylamino)ethoxy]-1H-indazole and oxalate thereof

A mixture of 1.7 gms. (0.0057 mole) of 1-benzyl-3-[(2-ethyl-2-amino)ethoxy]-1H-indazole, 4.2 gms. (0.052 mole) of 37% aqueous formaldehyde solution and 0.79 gms. (0.017 mole) of formic acid was refluxed for 18 hours with continuous stirring. The reaction mixture was cooled, made strongly basic with 30% aqueous sodium hydroxide solution (pH 12), and extracted with 10 mls. of benzene. The benzene layer was washed with water, dried over anhydrous sodium sulfate and the benzene distilled off under reduced pressure.

In this way, 1.9 gms. (corresponding to 100% yield) of the desired 1-benzyl-3-[(2-ethyl-2-dimethylamino)ethoxy]-1H-indazole was obtained in the form of a pale yellow viscous oil. A sample of the base was converted into the oxalate salt by treatment with oxalic acid in acetone/ethanol. The product, recrystallized from ethyl acetate/petroleum ether, had a melting point of 109° with decomposition.

| Elementary analysis: | | C(%) | H(%) | N(%) |
|---|---|---|---|---|
| | Calculated: | 63.91 | 6.58 | 10.16 |
| $C_{22}H_{27}N_3O_5$ | | | | |
| | Found: | 63.76 | 6.69 | 10.03 |

The 1-benzyl-3-[(2-ethyl-2-amino)ethoxy]-1H-indazole used as the starting compound for the alkylation reaction was obtained from 1-benzyl-3-[(2-ethyl-2-phthalimido)ethoxy]-1H-indazole by the following two-stage procedure.

Part A

1-Benzyl-3-[(2-ethyl-2-phthalimido)ethoxy]-indazole 17.83 Gms. (0.2 mole) of 2-aminobutan-1-ol was added, with stirring, to a suspension of 29.62 gms. (0.2 mole) of phthalic anhydride in 90 mls. of isopropanol. The resulting mixture was refluxed for 18 hours. Thereafter, the isopropanol was distilled off under reduced pressure and the residue was distilled to give 38.1 gms. (yield 87%) of 2-phthalimidobutan-1-ol as a colourless viscous oil. (boiling point = 170° to 172°C./1 mm. Hg.)

30 Gms. (0.14 mole) of 2-phthalimidobutan-1-ol so-obtained was added in portions to 12.35 gms. (0.046 mole) of phosphorous tribromide while maintaining the temperature between 5° to 10°C. The mixture was then heated at 100° for 1½ hours whereupon the hot reaction mixture was poured over crushed ice. The cool mixture was extracted with aliquots of ether and the combined ethereal extracts were washed with water and then dried over sodium sulfate. The ether was distilled off under reduced pressure and the residue was distilled to give a pale yellow viscous oil which solidified on standing. 18.7 Gms. of the desired product, 1-bromo-2-phthalimidobutane, were obtained. (boiling point = 175° to 184°/4 mm. Hg.)

1.2 Gms. (0.022 mole) of sodium methoxide were added to a solution of 5.0 gms. (0.022 mole) of 1-benzyl-3-hydroxy-1H-indazole in 25 ml. anhydrous dimethyl formamide, as solvent. Thereafter 6.29 gms. (0.022 mole) of 1-bromo-2-phthalimidobutane were added to the solution which was heated at 160° for 20 hours. The reaction mixture was then cooled to room temperature and diluted with 30 mls. of water and extracted with aliquots of benzene. The combined benzene extracts were washed with 5% aqueous sodium hydroxide solution, then with water and finally dried over sodium sulfate. The benzene was distilled off to give 5.5 gms. (yield = 58%) of the desired product in the form of a brown oil.

Part B

1-Benzyl-3-[(2-ethyl-2-amino)ethoxy]-1H-indazole 8.7 Gms. (0.02 mole) of 1-benzyl-3-[(2-ethyl-2-phthalimido)ethoxy]-1H-indazole obtained following the procedure of Part A and 2.05 gms. (0.04 mole) of hydrazine hydrate in ethanol were refluxed for 4 hours. Thereafter, 62 mls. of benzene were added to the suspension which had been cooled to 60°. This mixture was cooled further to room temperature whereupon the precipitate of phthalyl hydrazide which formed was removed by filtration. To the filtrate was added 82 mls. of water to effect an extraction. The aqueous phase, separated from the above, was further extracted with benzene. The benzene extracts were washed with 2% aqueous sodium hydroxide, water and then dried over anhydrous sodium sulfate. The benzene was distilled off to give 3.8 gms. (yield = 63%) of the desired 1-benzyl-3-[(2-ethyl-2-amino)ethoxy]-1H-indazole as a pale yellow viscous oil.

A sample of the base was converted into the hydrochloride salt by treatment with hydrogen chloride in a methanol/acetone mixture and crystallized for analysis from isopropanol.

Melting point: 213° to 215°

Elementary analysis:

| | | C(%) | H(%) | N(%) |
|---|---|---|---|---|
| $C_{19}H_{22}ClN_3O$ | Calculated: | 65.15 | 6.68 | 12.66 |
| | Found: | 65.15 | 6.71 | 12.92 |

EXAMPLE 2

1Benzyl-3-[(2-ethyl-2-dimethylamino)ethoxy]-5-chloro-1H-indazole and hydrochloride thereof A mixture comprising 4.6 g. (0.014 mole) of 1-benzyl-3-[(2-ehtyl-2-amino)ethoxy]-5-chloro-1H-indazole, 10 g. (0.124 mole) of 37% aqueous formaldehyde and 1.9 g. (0.0415 mole) of formic acid was refluxed for eighteen hours. The resulting solution was cooled and basified with 30% sodium hydroxide solution and the thoroughly extracted with benzene. The benzene extracts were combined, washed with water, dried and, finally, evaporated to give the desired product, which is a viscous oil, in a yield of 4.9 g. or 99% of theory.

A sample of the product was converted to the corresponding hydrochloride by treatment with methanolic hydrogen chloride, the salt so formed being recrystallized from methanol, melting point 170° –173°.

Elementary Analysis: Calculated for $C_{20}H_{25}Cl_2N_3OCH_3OH.H_2O$ C, 59.15 H, 6.85 C, 59.14; H, 6.72

The 1-benzyl-3-[(2-ethyl-2-amino)ethoxy]-5-chloro-1H-indazole used as the starting compound for the alkylation reaction was obtained from 1-benzyl-3-[(2-ethyl-2-phthalimido)ethoxy]-5-chloro-1H-indazole by the following two-stage procedure.

Part A

1-Benzyl-3-[(2-ethyl-2-phthalimido)ethoxy]-5-chloro-1H-indazole

A suspension was formed by adding 11 g. (0.039 mole) of 1-bromo-2-phthalimido-butane to a solution of 10.1 g. (0.039 mole) of 1-benzyl-3-hydroxy-5-chloro-1H-indazole and 2.1 g. (0.039 mole) of sodium methoxide in 47 ml. of dimethylformamide. The suspension was refluxed for 20 hours and the resulting solution cooled when 5.5 ml. of water was added. The so-formed mixture was extracted with several portions of benzene; the benzene extracts were combined and washed with 5% sodium hydroxide solution, then with water and, finally, dried. The benzene was distilled off to leave the desired product as a beige oil in a yield of 13.9 g. or 78% of theory. The compound was used without further treatment in Part B below.

Part B

1Benzyl-3-[(2-ethyl-2-amino)ethoxy]-5-chloro-1H-indazole

A mixture comprising 2,9 g. (0.0564 mole) of hydrazine hydrate and 12.9 g. (0.0282 mole) of 1-benzyl-3-[(2-ethyl-2-phthalimido)ethoxy]-5-chloro-1H-indazole and 109 ml. of ethanol was refluxed for four hours. The resulting suspension was cooled to 60°, 150 ml. of benzene added and then cooled to room temperature. The phthalyl hydrazide which precipitated was filtered off and discarded. The filtrate was mixed with 70 ml. of water; the organic (benzene) layer was separated and the aqueous layer extracted once with further benzene. The organic layer and benzene extract were combined and washed firstly with 2% sodium hydroxide solution and then with water and, finally, dried. The benzene was distilled off and the desired end product, a pale yellow oil obtained is a yield of 7.5 g. or 81% of theory.

A sample was converted into the corresponding hydrochloride salt by treatment with methanolic hydrogen chloride; the salt so formed was recrystallized from isopropanol water, and had a melting point of 251°–254°.

Elementary analysis: Calculated for $C_{18}H_{21}Cl_2N_3O$ C,59.02;H,5.78;Cl,19.36;N,11.47, Found C,58.72; H,6.04; Cl,19.52N,11.72.

Other compounds of the present invention are as follows:

1-benzyl-3-[(3-ethyl-3-dimethylamino)propoxy]-1H-indazole;

1-benzyl-3-[(3-ethyl-3-ethylmethylamino)propoxy]-5-chloro-1H-indazole;

1-benzyl-3-[(2-ethyl-2-diethylamino)ethoxy]-5-chloro-1H-indazole;

1-ethyl-3-[(2-ethyl-2-dimethylamino)ethoxy]-5-chloro-1H-indazole;

1-benzyl-3-[(2-ethyl-2-dihexylamino)ethoxy]-6-chloro-1H-indazole;

1-benzyl-3-[(2-hexyl-2-dimethylamino)ethoxy]-5-bromo-1H-indazole;

1-methyl-[(2-ethyl-2-dimethylamino)ethoxy]-6-bromo-1H-indazole

As referred hereinbefore it has been found in accordance with this invention that the tertiary aminoindazole compounds of the general formula I, and salts thereof, have interesting biologically purposes in that when the subject compounds are subjected to standard pharmacological evaluation they exhibit anti-inflammatory activity and also analgesic activity. The subject compounds used in this way can be used as anti-inflammatory drugs and/or treating certain symptoms of pain.

Accordingly, this invention further provides in another of its aspects a pharmaceutical composition comprising as an essential active ingredient at least one active compound of the general formula I or a salt thereof in association with a pharmaceutically acceptable carrier therefor.

The compositions of the present invention are preferably administered either orally or rectally. Advantageously, the composition is in a dosage unit form appropriate to the desired mode of administration. For example, the dosage unit may be a tablet, capsule, pill, powder, packet, granule, wafer, elixir, suppository, or a measured quantity of a suspension, solution, a syrup or segregated multiples of the foregoing. The term "dosage unit form: as used in the specification and claims refers to physically discrete units suitable as unitary dosages for human subjects and animals, each unit containing a predetermined quantity of active material calculated to produce the desired therapeutic effect in admixture, or otherwise in association, with a pharmaceutical carrier therefor, the quantity of the active ingredient being such that one or more units are normally required for a single therapeutic administration or that, in the case of severable units such as scored tablets, at least one fraction such as a half or a quarter of a severable unit is required for a single therapeutic administration.

Advantageously, the compositions of this invention contain the active ingredient in an amount of at least 0.5 and not more than 95% by weight based on the total weight of the composition. Conveniently, the compositions of the invention when in dosage unit form contain 0.5 mg. to 1000 mg., and more conveniently from 5 mg. to 250 mg., of the active ingredient of formula I.

The compositions of the present invention will normally consist of at least one compound of formula I; typically in the form of an acid addition, say, hydrochloride or maleate salt thereof admixed with a carrier, or diluted by a carrier, or enclosed or encapsulated by a carrier in the form of a capsule, sachet, catchet, paper or other container. A carrier which serves as a vehicle, excipient or diluent medium for the therapeutically active ingredient may be a solid, semisolid or a sterile liquid.

Some examples of the carriers which may be employed in the pharmaceutical compositions of the invention are lactose, dextrose, sorbitol, mannitol, starches such as wheat, corn or potato starch, gum acacia, calcium phosphate, liquid paraffin, cocoa butter, oil of theobroma, alginates, tragacanth, gelatin, syrup B.P., methyl cellulose, polyoxethylene sorbitan monolaurate, methyl and propyl hydroxybenzoates, pyrogen-free water and substantially isotonic saline solution. The choice of carrier is determined by the preferred form of administration, the solubility of the compound and standard pharmaceutical practice. In the case of tablets a lubricant may be incorporated to prevent sticking and binding of the powdered ingredients in the dies and on the punch of the tableting machine. For such purpose, there may be employed, for example, talc, aluminum, magnesium or calcium stearates or polyethylene glycols (Carbowaxes) of suitable molecular weight.

The pharmaceutical compositions of this invention may contain, in addition to the active ingredient of the general formula I, one or more other pharmacologically active ingredients which elicit desirable complementary effects.

Two examples of suitable pharmaceutical compositions according to this invention are presented below for the purpose of facilitating a better understanding of this aspect of the invention.

Example A

For oral administration, sugar coated tablets of the following composition were prepared following standard pharmaceutical practice.

| Formulation: Ingredient: | Content (mg.) |
| --- | --- |
| 1-Benzyl-3-[(2-ethyl-2-dimethylamino)ethoxy]-1H-indazole hydrochloride | 25 |
| Lactose | 60 |
| Starch | 50 |
| Sugar | 75 |
| Talc | 5 |
| Gum arabic | 5 |

Example B

Capsules were made by the procedure described below from a mixture of the following ingredients:

| Formulation: Ingredient: | Content (gms.) |
| --- | --- |
| 1-Benzyl-3-[2-ethyl-2-dimethylamino)ethoxy]-1H-indazole hydrochloride | 100 |
| Calcium phosphate | 20 |

Procedure:

The two powdered ingredients were thoroughly mixed together and filled into hard gelatin capsules so that each capsule contained 50 mg. of the active ingredient, 1-benzyl-3-[(2-ethyl-dimethylamino)ethoxy]-1H-indazole hydrochloride.

In the foregoing Examples A and B, the active ingredient specified may be wholly or partly replaced by another pharmacologically active compound of the invention.

The effectiveness and toxicity of typical compounds of this invention were determined by standard pharmacological tests. Thus, the analgesic activity was confirmed and evaluated by means of the acetylcholine induced writhing test in mice following basically the procedure of Siegmund et al. Proc. Soc. Exp. Biol., N.Y. 95:729, 1957, except that acetylcholine replaced phenylquinone as the antagonist, and/or utilizing pain electrosimultation on the tail of mice by the mouse tail clip test following basically the procedure of Bianchi and David J. Pharm. Pharmacology 1.12:499, 1960. The antiinflammatory activity was confirmed and evaluated by means of Carageenan Induced Edema in the hind paw of the rat following the method of Winter et al. Proc. Soc. Exp. Biol. & Med. 114, 544, 1962 and measured by the method of Singh & Ghosh, J. Pharm. Pharmacology 20, 316, 1968.

The compounds of the present invention also have anti-microbial activity and in a further aspect of the present invention there is provided anti-microbial compositions containing as anti-microbial agent a compound of formula I in combination with a suitable carrier.

While in the foregoing specification various embodiments of this invention have been set forth and specific details elaborated upon for the purpose of illustration, it will be apparent to those skilled in the art that this invention is susceptible to other embodiments and that many of the details may be varied widely without departing from the spirit and scope of the inention.

What we claim is:

1. A tertiary amino-indazole compound of formula I:

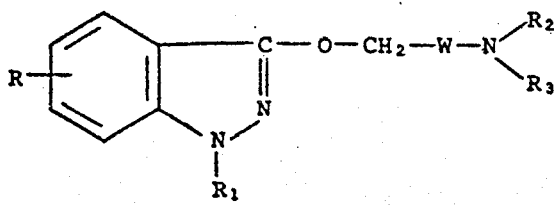

wherein

R is a hydrogen atom or a halogen atom;

$R_1$ is an alkyl group having 1 to 6 carbon atoms, or a phenyl alkyl group, the alkyl group having 1 to 6 carbon atoms;

$R_2$ and $R_3$ which may be the same or different and each is an alkyl group having 1 to 6 carbon atoms;

W is a branched chain alkylene group comprising a divalent straight chain lower alkyl group having 1 to 6 carbon atoms pendant from the beta or gamma carbon atom relative to the carbon atom;

or a non-toxic acid addition salt thereof.

2. A tertiary amino-indazole compound of formula I according to claim 1 wherein:

R is a hydrogen atom or a chlorine atom;

$R_1$ is an alkyl group having 1 to 6 carbon atoms;

$R_2$ and $R_3$, which may be the same or different, each represents a methyl group or an ethyl group; and, W is a group of the formula:

$$-CH-$$
$$\phantom{-}C_2H_5$$

3. A tertiary amino-indazole compound of formula I'

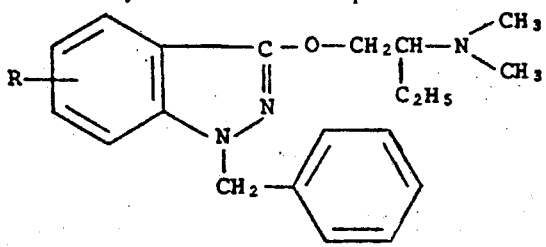

wherein

R is a hydrogen atom or a halogen atom which is in the 5- or 6- position, or a non-toxic acid addition salt thereof.

4. A tertiary amino-indazole compound of formula I' according to claim 3 wherein R is a hydrogen atom or a chlorine atom.

5. 1-Benzyl-3-[(2-ethyl-2-dimethylamino)-ethoxy]-1H-indazole or a non-toxic acid addition salt thereof.

6. 1-Benzyl-3-[(2-ethyl-2-dimethylamino)-ethoxy]-1H-indazole hydrochloride.

7. 1-Benzyl-3-[(2-ethyl-2-dimethylamino)-ethoxy]-5-chloro-1H-indazole or a non-toxic acid addition salt thereof.

8. 1-Benzyl-3-[(2-ethyl-2-dimethylamino)-ethoxy]-5-chloro-1H-indazole hydrochloride.

* * * * *